United States Patent [19]

Detty et al.

[11] 4,365,017

[45] Dec. 21, 1982

[54] TELLUROPYRYLIUM ELECTRON ACCEPTING DYE SENSITIZERS FOR ELECTRON DONATING PHOTOCONDUCTIVE COMPOSITIONS

[75] Inventors: Michael R. Detty; Bruce J. Murray; Jerome H. Perlstein, all of Rochester, N.Y.

[73] Assignee: Eastman Kodak Company, Rochester, N.Y.

[21] Appl. No.: 279,365

[22] Filed: Jul. 1, 1981

[51] Int. Cl.$^3$ .................... C07D 345/00; G03C 1/72
[52] U.S. Cl. ................................ 430/83; 260/239 R
[58] Field of Search ...................... 430/83; 260/239 R

[56] References Cited

U.S. PATENT DOCUMENTS 3,149,101  9/1964  Habel et al. .
3,542,764  11/1970  Mack .
3,971,742  7/1976  Gunther .

*Primary Examiner*—James R. Hoffman
*Attorney, Agent, or Firm*—John R. Everett

[57] ABSTRACT

Novel telluropyrylium dyes are disclosed. The dyes are useful as electron accepting sensitizers for electron donating photoconductive compositions. Novel methods making the dyes are also disclosed.

15 Claims, No Drawings

TELLUROPYRYLIUM ELECTRON ACCEPTING DYE SENSITIZERS FOR ELECTRON DONATING PHOTOCONDUCTIVE COMPOSITIONS

FIELD OF THE INVENTION

This invention relates to novel telluropyrylium electron accepting sensitizers, methods of making such dyes and their utility as electron acceptors in electron donating photoconductive compositions and elements.

BACKGROUND OF THE INVENTION

Pyrylium, thiapyrylium and selenapyrylium dyes are known. They are known to have a variety of uses including use as electron accepting sensitizers in electron donating photoconductive compositions.

No dyes comprising telluropyrylium nuclei, including benzotelluropyrylium nuclei, have been available for any use. No starting materials with which to make telluropyrylium dyes are described in the prior art.

SUMMARY OF THE INVENTION

The present invention provides novel dyes which comprise a telluropyrylium nucleus, including benzotelluropyrylium nucleus. The resulting dyes are useful as electron acceptors in increasing the sensitivity of organic photoconductive compositions containing electron donating photoconductors. Tertiary amines, such as triarylamine compounds, are examples of such photoconductors.

PREFERRED EMBODIMENTS

In a preferred embodiment the dyes of the present invention comprise a telluropyrylium nucleus having the structure:

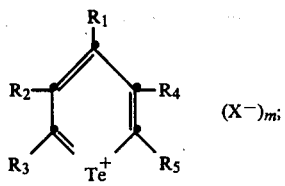   I.

wherein
$R_1$, $R_3$ and $R_5$ each independently represents hydrogen, alkyl, alkylamino, dialkylamino, alkoxy, aryloxy, alkylaryl, aryl, heterocyclyl,

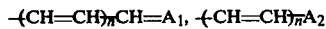

or a zwitterionic diketonate of the structure:

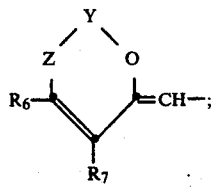   II.

wherein
$R_2$ and $R_4$ each independently represents hydrogen, aryl or alkyl; or
$R_2$ and $R_3$, or $R_4$ and $R_5$, taken together with the carbon atoms to which they are attached, form a mono- or polynuclear fused carbocyclic ring having from about 5 to 20 carbon atoms;
$R_6$ and $R_7$ each independently represents hydrogen, alkyl, aryl, heteroaryl or a mono- or polycyclic heterocyclylidene group, or $R_6$ and $R_7$ taken together with the carbon atom to which they are attached, form a fused mono- or polycyclic, carbocyclic or heterocyclic group having from about 5 to 20 carbon atoms;
$A_1$ represents a mono- or polycyclic heterocyclylidene group;
$A_2$ represents hydrogen, alkyl, alkoxy, aryl, amino, dialkylaminoaryl, alkylamino, arylamino, dialkylamino, diarylamino or a mono- or polycyclic heterocyclyl group;
n represents a number from 0 to 5;
m represents 1, except when $R_1$, $R_3$ or $R_5$ is the zwitterionic group, m represents 0;
X represents an anion;
Y represents $BF_2$ or $PF_4$; and
Z represents O or S.

In another preferred embodiment the dyes of this invention comprise a benzotelluropyrylium nucleus having the structure:

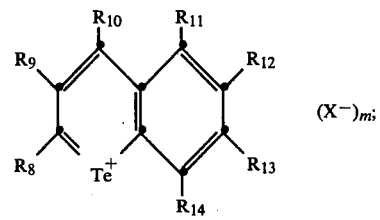   III.

$R_{10}$ and $R_8$ each independently represents hydrogen, alkyl, alkylamino, arylamino, alkoxy, aryloxy, dialkylamino, diarylamino,

or a zwitterionic diketonate of the structure:

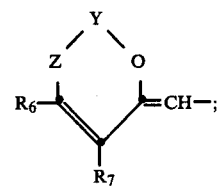   II.

$A_1$ represents a mono- or polycyclic heterocyclylidene group;
$A_2$ represents hydrogen, alkyl, alkoxy, aryl, amino, dialkylaminoaryl, alkylamino, arylamino, dialkylamino, diarylamino or a mono- or polycyclic heterocyclyl group;
$R_6$ and $R_7$ each independently represents hydrogen, alkyl, aryl, heteroaryl, a mono- or polycyclic heterocyclylidene group or $R_6$ and R taken together with the carbon atoms to which they are attached, form a fused mono- or polycyclic, carbocyclic or heterocyclic group having from about 5 to 20 carbon atoms;
$R_9$, $R_{11}$, $R_{12}$, $R_{13}$ and R each independently represents hydrogen, alkyl, alkoxy, aryl, halogen, alkylamino or arylamino; or
$R_{11}$ and $R_{12}$, $R_{12}$ and $R_{13}$ or $R_{13}$ and $R_{14}$, taken together with the carbon atoms to which they are attached, form a fused carbocyclic ring having from 5 to 20 carbon atoms;

n represents 0, 1 or 2;

m represents 1 except when $R_8$ or $R_{10}$ is the zwitterionic group, m represents 0;

X represents an anion;

Y represents $BF_2$ or $PF_4$; and

Z represents O or S.

In another preferred embodiment the dyes of this invention comprise a telluropyrylium nucleus having a structure according to Formula I wherein:

$R_1$, $R_3$ and $R_5$ each independently represents hydrogen, methyl, ethyl, phenyl, p-N,N-dimethylaminophenyl, p-anisyl, phenoxy, ethoxy, methoxy,

$R_6$ and $R_7$ each independently represents hydrogen, methyl, phenyl, methoxyphenyl, p-N,N-dimethylaminophenyl, pyridyl, oxazolyl, thiazolyl, selenazolyl, pyranyl, thiapyranyl, selenapyranyl, telluropyranyl, or oxaindolazinyl or $R_6$ and $R_7$ are taken together with the carbon atoms to which they are attached to form a fused mono- or polycyclic, carbocyclic or heterocyclic group having from 5 to 20 carbon atoms;

$A_1$ represents a nucleus selected from the group consisting of oxazolylidene, thiazolylidene, selenazolylidene, imidazolylidene, pyranylidene, thiapyranylidene, selenapyranylidene, telluropyranylidene, oxaindolazinylidene, benzoxazolylidene, benzothiazolylidene, benzopyranylidene, benzothiapyranylidene, benzoselenapyranylidene, or benzotelluropyranylidene;

$A_2$ represents hydrogen, methyl, methoxy, ethoxy, phenyl, dimethylaminophenyl, dimethylamino or a nucleus selected from the group consisting of oxazolyl, 9-julolidyl, thiazolyl, selenazolyl, imidazolyl, pyryliumyl, thiapyryliumyl, selenapyrylium, telluropyrylium, pyrydinyl, furanyl, thiophenyl, selenophenyl, tellurophenyl, oxaindolazinyl, benzoxazolyl, benzothiazolyl, benzopyryliumyl, benzothiapyryliumyl, benzoselenapyryliumyl, benzotelluropyryliumyl or naphthyl;

X represents $BF_4$, $ClO_4$, $CF_3SO_3$, $FSO_3$, $PF_6$, $CH_3SO_3$, CL, Br, or I.

In another preferred embodiment, the dyes of this invention comprise a benzotelluropyrylium nucleus and a structure according to formula III wherein:

$R_8$ and $R_{10}$ each independently represents hydrogen, methyl, ethyl, methoxy, hydroxy, ethoxy, phenyl, phenoxy, p-anisyl, 2,5-dimethoxy- phenyl, p-N,N-dimethylaminophenyl,

$A_1$ represents a nucleus selected from the group consisting of oxazolylidene, thiazolylidene, selenazolylidene, imidazolylidene, pyranylidene, thiapyranylidene, selenapyranylidene, telluropyranylidene, oxaindolazinylidene, benzoxazolylidene, benzothiazolylidene, benzopyranlidene, benzothiapyranylidene, benzoselenapyranylidene, or benzotelluropyranylidene;

$A_2$ represents methyl, methoxy, ethoxy, phenyl, dimethylaminophenyl, dimethylamino or a nucleus selected from the group consisting of oxazolyl, 9-julolidyl, thiazolyl, selenazolyl, imidazolyl, pyryliumyl, thiapyryliumyl, selenapyrylium, telluropyrylium, pyrydinyl, furanyl, thiophenyl, selenophenyl, tellurophenyl, oxaindolazinyl, benzoxazolyl, benzothiazolyl, benzopyryliumyl, benzothiapyryliumyl, benzoselenapyryliumyl, benzotelluropyryliumyl or naphthyl;

$R_7$ and $R_6$ each independently represents hydrogen, methyl, phenyl, methoxyphenyl, p-N,N-dimethylaminophenyl, aminophenyl, pyridyl, oxazolyl, thiazolyl, selenazolyl, pyranyl, thiapyranyl, selenapyranyl, telluropyranyl or oxindolazinyl; or $R_6$ and $R_7$ are taken together with the carbon atom to which they are attached to form a fused naphthalene ring; and X represents $BF_4$, $ClO_4$, $CF_3SO_3$, $FSO_3$, $PF_6$, $CH_3SO_3$, Cl, Br or I.

Heteroaryl, heterocyclic and heterocyclidene groups contain hetero atoms such as O, P, N, S, Se and Te. Examples of the latter groups include the groups generally used to form cyanine dyes, such as pyridyl, furaryl, thiopyranyl, selenopyranyl, telluropyranyl, oxazolyl, thiazolyl, selenazolyl, tellurazolyl, benzoxazolyl, benzthiazolyl, benzselenazolyl, and benztellurazolyl. "Alkyl" refers to a branched- or straight-chain hydrocarbon having up to 16 carbon atoms, such as methyl, butyl, dodecyl, nonyl and isobutyl; "aryl" refers to phenyl, naphthyl and anthryl. Heteroaryl, heterocyclidene, alkyl and aryl are optionally further substituted with substituents such as allyl, aryl, halogen, nitro, cyano, carboxy, hydroxy, alkoxy, aryloxy, aralkyl, acyl, amide, sulfonamide, dialkylamino and amino.

The dyes of this invention are prepared with telluropyrone and benzotelluropyrone intermediates.

The telluropyrone intermediates are prepared according to copending commonly assigned U.S. patent application Ser. No. 279,361, entitled "Mononuclear Telluropyrone Compositions of Matter" in the name of Detty et al and having the same filing date of the present case.

In general the method of preparation involves admixing an alkyl alcohol solution containing a telluride dianion and an alkoxide anion with a solution containing a pentadiynone wherein the pentadiynone has the structure:

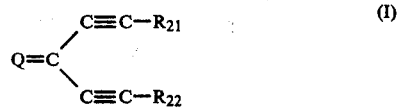

and the resulting composition of matter has a mononuclear telluropyrone nucleus having the structure:

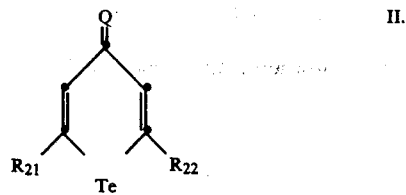

wherein $R_{21}$ and $R_{22}$ each independently represents aryl, a monocyclic or polycyclic heteroaromatic group, alkyl, alkoxy, amino, trialkylsiloyl, triarylsilyl, alkylamino, dialkylamino or halogen;

Q represents O, S or Se.

"Aryl", which is substituted or unsubstituted, refers to substituents such as phenyl, naphthyl, anthryl, methoxyphenyl, alkoxy phenyl, dialkylamino phenyl, alkylphenyl, nitrophenyl and halophenyl. "Alkyl" and alkoxy refer to a branched- or straight-chain hydrocarbon having up to 16 carbon atoms, such as methyl, ethyl, propyl, isopropyl, butyl, dodecyl, nonyl and isobutyl. Mono- and polycyclic heteroaromatic groups refer to aromatic groups having hetero atoms such as O, S, Se and Te. Examples of the latter groups include the groups normally used to form cyanine dyes, such as pyridyl, furaryl, thiophenyl, selenophenyl, tellurophenyl, oxazolyl, thiazolyl, selenazolyl, tellurazolyl, benzoxazolyl, benzthiazolyl, benzselenazolyl, and benztellurazolyl.

Substituents on alkyl, aryl and heteroaromatic groups include alkyl, aryl, halogen, nitro, cyano, carboxy, hydroxy, alkoxy, amido, aryl, amino, alkylamino, dialkylamino, trialkylsilyl, alkylarylsilyl, triarylsilyl, alkylthio, arylthio, and aryloxy.

The benzotelluropyrone intermediates are prepared according to the teachings of copending commonly assigned U.S. patent application Ser. No. 279,300, entitled "Substituted Benzotelluropyrone Compositions of Matter," in the name of Detty et al and having the same filing date as the present case. In general the method of preparation involves cyclizing a 3-aryltelluroacrylic acid or a 3-aryltelluroacryloyl halide, wherein (a) the aryltelluroacrylic acid or 3-aryltelluroacryloyl halide has the structure:

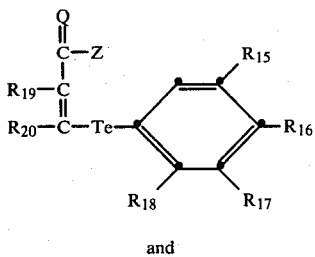

(I)

and (b) the resulting benzotelluropyrone has the structure:

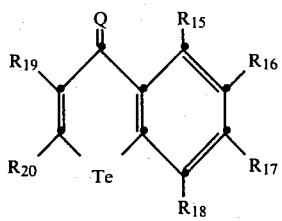

(II)

in which structures, $R_{19}$ and $R_{20}$ each independently represents hydrogen, alkyl, alkoxy, halogen and aryl, or together with the carbon atoms to which they are attached form a carbocyclic or heterocyclic fused ring structure having about 5 to 20 carbon atoms;

$R_{15}$ and $R_{17}$ each independently represents an electron donating group, hydrogen, halogen, alkyl or aryl; provided that at least one of $R_{15}$ and $R_{17}$ is an electron donating group, such as hydroxy, alkoxy, aryloxy, amino, dialkylamino, alkylazo, arylazo, halogen, alkylthio or arylthio;

$R_{16}$ and $R_{18}$ each independently represents hydrogen and halogen, alkyl, or $R_{16}$ and $R_{17}$, or $R_{17}$ and $R_{18}$, together with the carbon atoms to which they are attached form a mono- or polycyclic, carbocyclic or heterocyclic fused ring structure having 5 to 20 carbon atoms;

Q represents O, S or Se; and

Z represents OH, BR, Cl or I;

The starting materials are cyclized by contact with a Friedel-Crafts catalyst in a halogenated solvent such as methylene chloride, preferably in an inert atmosphere. The temperature of the solution is maintained at or below 0° C. From 0.1 to 1.1 equivalents of the selected Friedel-Crafts catalyst are added to the solution. The temperature of the solution is raised to about 20° C. to 40° C. to allow the reaction to proceed to formation of the novel benzotelluropyrone compositions of matter, including benzotelluropyrone thiones. After the reaction is completed, the reaction mixture is cooled to room temperature.

The starting materials are also cyclized by contact with a solution of phosphorous pentoxide in methane sulfonic acid. The contact is carried out by adding a solution consisting of from about 5.0 to 10.0 percent by weight of phosphorous pentoxide in methane sulfonic acid, to 0.1 to 0.5 molar equivalents of the starting materials.

The telluropyrones and benzotelluropyrones are converted to the corresponding telluropyryliums and benzotelluropyryliums by the known methods for converting pyrones to pyryliums. Among such methods are the techniques:

(1) condensing a telluropyrone or benzotelluropyrone with an active methyl compound of another heterocyclic group in a dehydrating medium such as acetic anhydride.

(2) adding a Grignard reagent to the carbonyl of a telluropyrone or telluroflavone and treating the intermediate alcohol with an acid HX wherein X is as previously defined. (See Example 4).

(3) adding an alkyl sulfonate such as methylfluorosulfonate or ethylfluorosulfonate to a telluropyrone or telluroflavone. (See Example 2).

(4) reducing the carbonyl or thione of a telluropyrone or telluroflavone with a reducing agent such as diisobutylaluminum hydride and treating the intermediate alcohol with an acid HX with X as indicated. This method was used in Example 1 to prepare Dye 2 of Table II.

The telluropyrylium dyes including benzotelluropyrylium dyes obtained according to the foregoing procedures are easily converted to other telluropyrylium dyes using known methods, such as:

(1) condensing an active methyl of a telluropyrylium or a benzotelluropyryliums with a 1,1-"dialdehyde" equivalent (e.g., ethyl orthoformate), 1,3-dialdehyde equivalent (e.g., 1,3,3-trimethoxypropene), or a 2-ene-1,5-dialdehyde equivalent (e.g., glutacondialdehyde dianil hydrochloride) in a dehydrating medium such as acetic acid-acetic anhydride in the present of a base such as pyridine, sodium acetate, and the like. (See Example 5).

(2) condensing an active methyl compound of the telluropyryliums with an aldehyde or ketone in a dehydrating medium such as acetic anhydride.

(3) forming and decomposing a Meldrum's acid adduct of a telluropyrone or telluroflavone with an acid HX. (See Example 3).

Tables I, II and III disclose a representative portion of the dyes made according to one or more of the above disclosed procedures. The structure of all dyes was confirmed by NMR analysis, infrared spectral analysis, mass spectral analysis and elemental analysis.

TABLE I

Telluropyrylium Dyes having the structures:

IV.

$$\text{structure IV: Te}^+ \text{ ring with } R_3, R_5 \text{ substituents, } -(CH=CH)_n-A_2, X^-$$

and

V.

$$\text{structure V: Te}^+ \text{ ring with } R_3, R_5 \text{ substituents, } -(CH=CH)_n-CH=A_1, X^-$$

| Dye No. | =A₁ or —A₂ | R₃ | R₅ | n | X⁻ |
|---|---|---|---|---|---|
| 1 | p-Me₂N—C₆H₄— | C₆H₅ | C₆H₅ | 0 | ClO₄ |
| 2 | p-Me₂N—C₆H₄— | C₆H₅ | C₆H₅ | 0 | BF₄ |
| 3 | p-Me₂N—C₆H₄— | C₆H₅ | C₆H₅ | 0 | CF₃SO₃ |
| 4 | Ph—(O ring)—Ph (=) | C₆H₅ | C₆H₅ | 1 | BF₄ |
| 5 | Ph—(S ring)—Ph (=) | C₆H₅ | C₆H₅ | 1 | ClO₄ |
| 6 | Ph—(Se ring)—Ph (=) | C₆H₅ | C₆H₅ | 1 | ClO₄ |
| 7 | CH₃CH₂O— | C₆H₅ | C₆H₅ | 0 | FSO₃ |
| 8 | CH₃— | C₆H₅ | C₆H₅ | 0 | BF₄ |
| 9 | Ph—(Te ring)—Ph (=) | C₆H₅ | C₆H₅ | 1 | BF₄ |
| 10 | Ph—(O ring)—Ph (=) | C₆H₅ | C₆H₅ | 0 | BF₄ |
| 11 | Ph—(S ring)—Ph (=) | C₆H₅ | C₆H₅ | 0 | ClO₄ |
| 12 | Ph—(Se ring)—Ph (=) | C₆H₅ | C₆H₅ | 0 | ClO₄ |
| 13 | Ph—(Te ring)—Ph (=) | C₆H₅ | C₆H₅ | 0 | BF₄ |
| 14 | p-Me₂N—C₆H₄— | C₆H₅ | C₆H₅ | 1 | BF₄ |
| 15 | p-Me₂N—C₆H₄— | C₆H₅ | C₆H₅ | 2 | BF₄ |
| 16 | (julolidine group) | C₆H₅ | C₆H₅ | 1 | CF₃SO₃ |
| 17 | (tetrahydroquinoline group) | C₆H₅ | C₆H₅ | 1 | CF₃SO₃ |
| 18 | CH₃— | C₆H₅ | C₆H₅ | 0 | BF₄ |
| 19 | CH₃CH₂O— | C₆H₅ | C₆H₅ | 0 | FSO₃ |
| 20 | p-Me₂N—C₆H₄— | CH₃ | CH₃ | 0 | BF₄ |

TABLE II

Benzotelluropyrylium dyes having the structure:

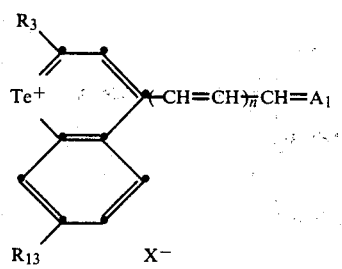

VI.

and

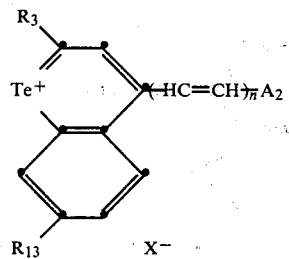

VII

TABLE II-continued

Benzotelluropyrylium dyes having the structure:

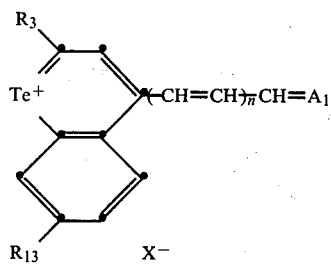

VI.

and

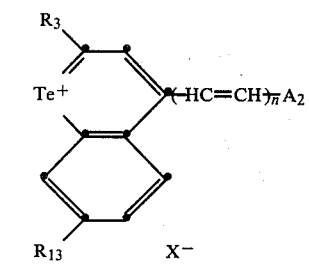

VII

| Dye No. | =$A_1$ or —$A_2$ | $R_3$ | $R_{13}$ | n | $X^-$ |
|---|---|---|---|---|---|
| 1 | H | $C_6H_5$ | $CH_3O$ | 0 | $ClO_4$ |
| 2 | H | $C_6H_5$ | $CH_3O$ | 0 | $PF_6$ |
| 3 | $CH_3$— | $C_6H_5$ | $CH_3O$ | 0 | $CF_3SO_3$ |
| 4 | $CH_3$— | $C_6H_5$ | $CH_3O$ | 0 | $BF_4$ |
| 5 | $CH_3$— | $C_6H_5$ | $CH_3O$ | 0 | $ClO_4$ |
| 6 | $CH_3$— | $C_6H_5$ | $CH_3O$ | 0 | $ClO_4$ |
| 7 | $CH_3CH_2O$— | $C_6H_5$ | $CH_3O$ | 0 | $FSO_3$ |
| 8 | $CH_3CH_2O$— | $CH_3$ | $CH_3O$ | 0 | $FSO_3$ |
| 9 | p-$Me_2N$—$C_6H_4$— | $C_6H_5$ | $CH_3O$ | 0 | $BF_4$ |
| 10 | p-$Me_2N$—$C_6H_4$— | $C_6H_5$ | $CH_3O$ | 0 | $ClO_4$ |
| 11 | p-$Me_2N$—$C_6H_4$— | $C_6H_5$ | $CH_3O$ | 1 | $CF_3SO_3$ |
| 12 | p-$Me_2N$—$C_6H_4$— | $C_6H_5$ | $CH_3O$ | 1 | $BF_4$ |
| 13 | p-$Me_2N$—$C_6H_4$— | $C_6H_5$ | $CH_3O$ | 2 | $CF_3SO_3$ |
| 14 | $Me_2N$— | $C_6H_5$ | $CH_3O$ | 1 | $CF_3SO_3$ |
| 15 | Ph—(O, Ph)= | $C_6H_5$ | $CH_3O$ | 0 | $BF_4$ |
| 16 | Ph—(S, Ph)= | $C_6H_5$ | $CH_3O$ | 0 | $ClO_4$ |
| 17 | Ph—(Se, Ph)= | $C_6H_5$ | $CH_3O$ | 0 | $ClO_4$ |
| 18 | 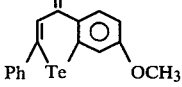 | $C_6H_5$ | $CH_3O$ | 1 | $CF_3SO_3$ |
| 19 | 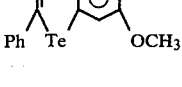 | $C_6H_5$ | $CH_3O$ | 1 | $ClO_4$ |
| 20 | 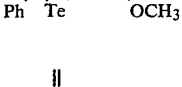 | $C_6H_5$ | $CH_3O$ | 1 | $PF_6$ |
| 21 | 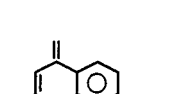 | $C_6H_5$ | $CH_3O$ | 1 | $CF_3SO_3$ |
| 22 | 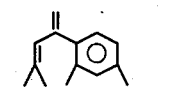 | $C_6H_5$ | $CH_3O$ | 2 | $PF_6$ |
| 23 | 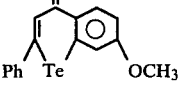 | $C_6H_5$ | $CH_3O$ | 2 | $CF_3SO_3$ |
| 24 | 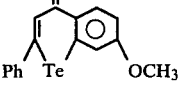 | $C_6H_5$ | $CH_3O$ | 3 | $CF_3SO_3$ |

TABLE II-continued

Benzotelluropyrylium dyes having the structure:

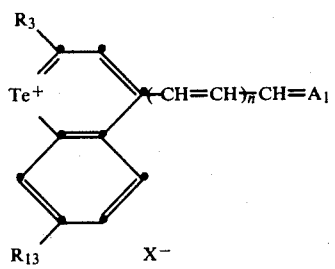

VI.

and

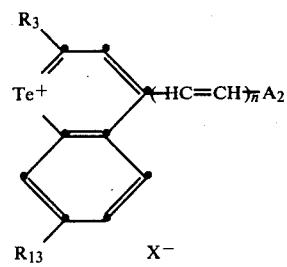

VII

| Dye No. | =A₁ or —A₂ | R₃ | R₁₃ | n | X⁻ |
|---|---|---|---|---|---|
| 25 | 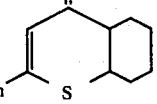 | C₆H₅ | CH₃O | 1 | CF₃SO₃ |
| 26 | 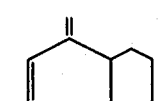 | C₆H₅ | CH₃O | 2 | CF₃SO₃ |
| 27 | 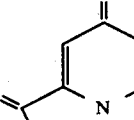 | C₆H₅ | CH₃O | 1 | BF₄ |
| 28 | 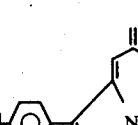 | C₆H₅ | CH₃O | 1 | BF₄ |
| 29 |  | C₆H₅ | CH₃O | 1 | PF₆ |

TABLE II-continued

Benzotelluropyrylium dyes having the structure:

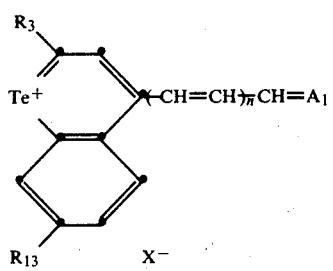

VI.

and

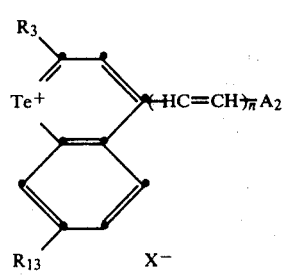

VII

| Dye No. | =A₁ or —A₂ | R₃ | R₁₃ | n | X⁻ |
|---|---|---|---|---|---|
| 30 | C₆H₅— | CH₃ | CH₃O | 0 | CF₃SO₃ |
| 31 | C₆H₅— | p-Me₂N—C₆H₄ | CH₃O | 1ᵃ | CF₃SO₃ |
| 32 | p-Me₂N—C₆H₄— | CH₃CH₂O | CH₃O | 1ᵃ | FSO₃ |
| 33 | p-Me₂N—C₆H₄— | CH₃CH₂O | CH₃O | 2ᵃ | FSO₃ |
| 34 | 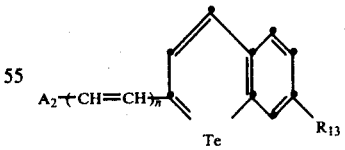 | CH₃CH₂O | CH₃O | 1ᵃ | FSO₃ |
| 35 | 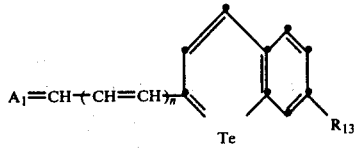 | CH₃CH₂O | CH₃O | 0ᵃ | FSO₃ |

ᵃthese compounds refer to the following structures:

$A_2\text{---CH=CH}_{\overline{n}}$ [structure with Te, R₁₃]

and $A_1\text{=CH---CH=CH}_{\overline{n}}$ [structure with Te, R₁₃]

TABLE III

Telluropyrylium dyes having zwitterionic diketonate substituents. In this table, Ph represents phenyl.

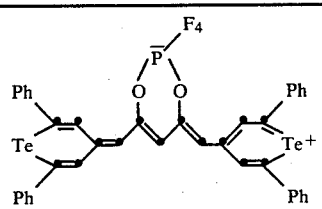
1

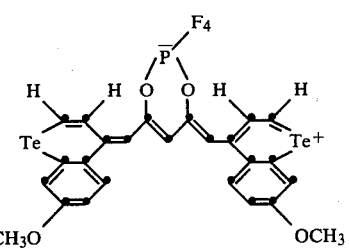
2

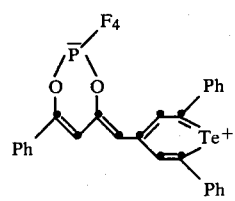
3

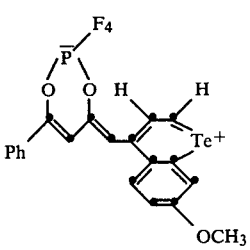
4

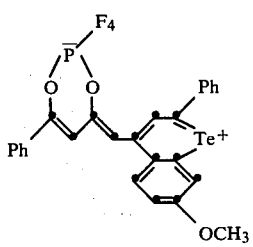
5

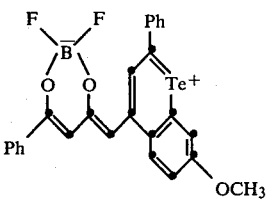
6

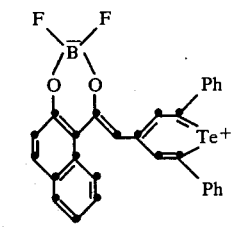
7

TABLE III-continued

Telluropyrylium dyes having zwitterionic diketonate substituents. In this table, Ph represents phenyl.

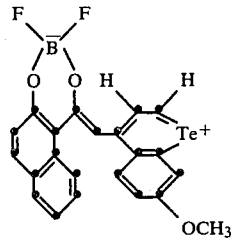
8

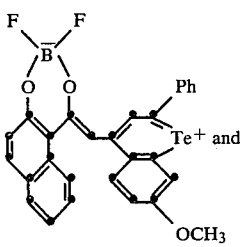
9

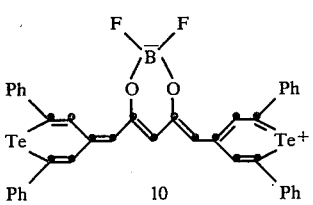
10

The present invention provides photoconductive compositions and elements in which organic electron donor-type photoconductors are combined with sensitizing amounts of the electron accepting dyes of the present invention.

The compositions are generally prepared by blending a dispersion or solution of the donor-type photoconductor together with an electrically insulating, film-forming resin binder, when necessary or desirable, and coating the compositions on a support or forming a self-supporting layer with the photoconductive composition. Generally, a sensitizing amount of the dye compound is mixed with the photoconductive coating composition so that, after thorough mixing, the sensitizing dye is uniformly distributed throughout a layer formed from the composition. The amount of dye which can be added to a photoconductive composition layer to give effective increases in sensitivity vary widely. The optimum concentration in any given case varies with the specific donor and salt acceptor used.

In general, an appropriate dye is added in a concentration range from about 0.001 to about 30 percent by weight based on the weight of the film-forming coating composition. Generally, the dye is added to the coating composition in an amount from about 0.05 to about 10 percent by weight of the total coating composition.

The dyes used in this invention are effective for enhancing the photosensitivity of a wide variety of donor-type photoconductors especially those containing a tertiary amine component. Useful photoconductors are described below.

(1) arylamine photoconductors including substituted and unsubstituted arylamines, diarylamines, nonpolymeric triarylamines and polymeric triarylamines such as those described in U.S. Pat. Nos.

3,240,597 by Fox issued Mar. 15, 1966, and 3,180,730 by Klupfel et al issued Apr. 27, 1965;

(2) polyarylalkane photoconductors of the types described in U.S. Pat. Nos. 3,274,000 by Noe et al issued Sept. 20, 1966, 3,542,547 by Wilson issued Nov. 24, 1970, and 3,542,544 by Seus et al issued Nov. 24, 1970;

(3) 4-diarylamino-substituted chalcones of the types described by Fox, U.S. Pat. No. 3,526,501 issued Sept. 1, 1970;

(4) nonionic cycloheptenyl compounds of the types described by Looker, U.S. Pat. No. 3,533,786 issued Oct. 13, 1970;

(5) compounds containing an:

nucleus, as described by Fox, U.S. Pat. No. 3,542,546 issued Nov. 24, 1970;

(6) organic compounds having a 3,3'-bisaryl-2-pyrazoline nucleus, as described by Fox et al, U.S. Pat. No. 3,527,602 issued Sept. 8, 1970;

(7) triarylamines in which at least one of the aryl radicals is substituted by either a vinyl radical or a vinylene radical having at least one active hydrogen-containing group, as described by Brantly et al, U.S. Pat. No. 3,567,450 issued Mar. 2, 1971;

(8) triarylamines in which at least one of the aryl radicals is substituted by an active hydrogen-containing group, as described by Brantly et al, Belgian Pat. No. 728,563 dated Apr. 30, 1969;

(9) any other organic donor compound which exhibits photoconductive properties such as those set forth in Australian Pat. No. 248,402 and the various polymeric photoductors such as the photoconductive carbazol polymers described in U.S. Pat. No. 3,421,891 issued Jan. 14, 1969.

Preferred binders for use in preparing the photoconductive layers which can be sensitized in accordance with the method of this invention comprise polymers having high dielectric strength which are good electrically insulating film-forming vehicles.

Materials of this type comprise styrene-butadiene copolymers; silicone resins; styrene-alkyd resins; silicone-alkyd resins; soyaalkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetals) such as poly(vinyl butyral); polyacrylic and methacrylic esters such as poly(methyl methacrylate), poly(n-butyl methacrylate), poly(isobutyl methacrylate), etc.; polystyrene; nitrated polystyrene; polymethylstyrene; isobutylene polymers; polyesters such as poly(ethylene alkylenebis(aryleneoxyalkylene) terephthalate) such as poly(ethylene-co-2,2'-isopropylidenebisphenyleneoxymethylene) terephthalate; phenolformaldehyde resins; ketone resins; polyamides; polycarbonates; polythiocarbonates; 2,2'-isopropylidenebis(phenyleneoxyethylene); nuclear-substituted poly(vinyl haloarylates), etc.

Methods of making resins of this type have been described in the prior art; for example, styrene-alkyd resins are prepared according to the method described in U.S. Pat. Nos. 2,361,019 and 2,258,423. Suitable resins of the type contemplated for use in the photoconductive layers of the invention are sold under such trademarks as Vitel PE-101, Cymac, Piccopale 100, Saran F-220 and Lexan 105 and 145. Other types of binders which are useful in the photoconductive layers of the invention include such materials as paraffin and mineral waxes. If a polymeric photoconductor is used, the binder may be omitted.

The organic coating solvents useful for preparing coating dopes are selected from a variety of materials. Useful liquids are hydrocarbon solvents, including substituted hydrocarbon solvents, with preferred materials being halogenated hydrocarbon solvents. The requisite properties of the solvent are that it be capable of dissolving the acceptor and capable of dissolving or at least highly swelling or solubilizing the polymeric ingredient of the composition. In addition, it is helpful if the solvent is volatile, preferably having a boiling point of less than about 200° C. Particularly useful solvents include halogenated lower alkanes having from 1 to about 3 carbon atoms such as dichloromethane, dichloroethane, dichloropropane, trichloromethane, trichloroethane, tribromomethane, trichlorofluoromethane, trichlorotrifluoroethane, etc.; aromatic hydrocarbons such as benzene, toluene, as well as halogenated benzene compounds such as chlorobenzene, bromobenzene, dichlorobenzene, etc.; ketones such as dialkyl ketones having 1 to about 3 carbon atoms in the alkyl moiety such as dimethyl ketone, methyl ethyl ketone, etc.; and ethers such as tetrahydrofuran, etc. Mixtures of these and other solvents are also useful.

In preparing the photoconductive coating composition, useful results are obtained where the donor is present in an amount equal to at least about 1 weight percent of the coating composition. The upper limit in the amount of donor present is widely varied in accordance with usual practice. In those cases where a binder is employed, it is generally required that the donor be present in an amount from about 1 weight percent of the coating composition to about 99 weight percent of the coating composition. A polymeric donor can be employed, in which case an additional binder may not be required. A preferred weight range for the donor substance in the coating composition is from about 10 weight percent to about 60 weight percent.

Suitable supporting materials for coated photoconductive layers which are sensitized in accordance with the method of this invention can include any of a wide variety of electrically conducting supports, for example, paper (at a relative humidity above 20 percent); aluminum-paper laminates; metal foils such as aluminum foil and zinc foil; metal plates such as aluminum, copper, zinc, brass and galvanized plates; vapor-deposited metal layers such as silver, nickel and aluminum coated on paper or conventional photographic film bases such as cellulose acetate and polystyrene. Such conducting materials as nickel can be vacuum-deposited on transparent film supports in sufficiently thin layers to allow electrophotographic elements prepared therewith to be exposed from either side of such elements. An especially useful conducting support is prepared by coating a support material such as poly(ethylene terephthalate) with a conducting layer containing a semiconductor dispersed in a resin. Such conducting layers both with and without insulating barrier layers are described in U.S. Pat. No. 3,245,833. Likewise, a suitable conducting coating can be prepared from the sodium salt of a carboxyester lactone of maleic anhydride and a vinyl acetate polymer. Such kinds of conducting layers and methods for their optimum preparation and use are disclosed in U.S. Pat. Nos. 3,007,901 and 3,262,807.

Coating thicknesses of the photoconductive composition on the support can vary widely. Generally, a coating in the range of about 10 microns to about 300 microns before drying is useful for the practice of this invention. The preferred range of coating thickness is found to be in the range from about 50 microns to about 150 microns before drying, although useful results are obtained outside this range. The resultant dry thickness of the coating is preferably between about 2 microns and about 50 microns, although useful results are obtained with a dry coating thickness between about 1 and about 200 microns.

The photoconductive compositions and elements of the present invention are employed in any of the well-known electrophotographic processes which require photoconductive layers and elements. In one such process, a photoconductive element is held in the dark and given a blanket electrostatic charge by placing it under a corona discharge. This uniform charge is retained by the layer because of the substantial dark insulating property of the layer, i.e., the low conductivity of the layer in the dark. The electrostatic charge formed on the surface of the photoconductive layer is then selectively dissipated from the surface of the layer by imagewise exposure to light by means of a conventional exposure operation, for example, by a contact-printing technique, or by lens projection of an image to form a latent electrostatic image in the photoconductive layer. Exposing the surface in this manner forms a pattern of electrostatic charge by virtue of the fact that light energy striking the photoconductor causes the electrostatic charge in the light-struck areas to be conducted away from the surface in proportion to the intensity of the illumination in a particular area.

The charge pattern produced by exposure is then developed or transferred to another surface and developed there, i.e., either the charged or uncharged areas rendered visible, by treatment with a medium comprising electrostatically responsive particles having optical density. The developing electrostatically responsive particles can be in the form of a dust, i.e., powder, or a pigment in a resinous carrier, i.e., toner. A preferred method of applying such toner to a latent electrostatic image for solid area development is by the use of a magnetic brush. Methods of forming and using a magnetic brush toner applicator are described in U.S. Pat. Nos. 2,786,439 by Young, 2,786,440 by Giaimo and 2,786,441 by Young, all issued Mar. 26, 1957, and 2,874,063 by Greig issued Feb. 17, 1959. Liquid development of the latent electrostatic image is also useful. In liquid development, the developing particles are carried to the image-bearing surface in an electrically insulating liquid carrier. Methods of development of this type are widely known and have been described in the patent literature, for example, Metcalfe et al, U.S. Pat. No. 2,907,674 issued Oct. 6, 1959. In dry developing processes, the most widely used method of obtaining a permanent record is achieved by selecting a developing particle which has as one of its components a low-melting resin. Heating the powder image then causes the resin to melt or fuse into or on the element. The powder is, therefore, caused to adhere permanently to the surface of the photoconductive layer. In other cases, a transfer of the electrostatic charge image formed on the photoconductive layer is made to a second support such as paper which then becomes the final print after development and fusing. Techniques of the type indicated are well-known in the art and have been described in the literature in *RCA Review*, Volume 15 (1954), pages 469–484.

The following examples are presented to further illustrate this invention.

EXAMPLE 1

Preparation of Dye 2, Table II
(7-Methoxy-benzotelluropyrylium Hexafluorophosphate)

Ten ml of a 22% w/w solution of diisobutylaluminum hydride (w/w) in hexane was added to a slurry of 1.81 g of 7-methoxybenzotelluropyrone in 20 ml of toluene cooled to 0° C. The cooling bath was removed and the reaction mixture was warmed to ambient temperature. Twenty ml of 1 N sodium hydroxide was added. The resulting mixture was stirred for 1 hour at ambient temperature and was then diluted with 100 ml of ether. The organic phase was washed with brine and concentrated. The residue was dissolved in 25 ml of acetic acid and 2 ml of hexafluorophosphoric acid was added. Upon cooling, a red solid precipitated. The precipitate was filtered, washed with ether and dried.

EXAMPLE 2

Preparation of Dye 7, Table II
(4-Ethoxy-7-methoxybenzotelluropyrone Fluorosulfonate Five g of 7-methoxybenzotelluropyrone was added to 20 ml of freshly distilled ethyl fluorosulfonate. The resulting mixture was stirred under nitrogen at 60° C. for 10 minutes. Two hundred ml of ether was added precipitating a red solid. The product was collected by filtration and recrystallized from acetonitrile to give 6.0 g (87%) of a red solid.

EXAMPLE 3

Preparation of Dye 3, Table II
4-Methyl-7-methoxybenzotelluropyrylium Trifluoromethanesulfonate Meldrum's acid (0.29 g) was dissolved in 10 ml of pyridine. The 4-ethoxy-7-methoxybenzotelluropyrylium fluorosulfonate (1.0 g, 2.0 mmol) was added as a powder immediately giving a dark red solution. The solution was concentrated in vaccuo. The residue was purified by chromatography on silica gel eluting with methylene chloride to give 0.90 g (92%) of a red solid.

The red solid (22.0 g, 0.0449 mol) was dissolved in 440 ml of 97% formic acid. The reaction mixture was stirred with steam bath heating until gas evolution ceased. Trifluoromethane sulfonic acid (8.4 g, 0.056 mol) was added and the reaction mixture was concentrated in vaccuo. Ether (400 ml) was added precipitating 18.4 g (80%) of a red solid. The crude product was dissolved in acetonitrile and precipitated with ether to give 13.8 g (60%) of material.

EXAMPLE 4

Preparation of Dye 1, Table I
4-(p-N,N-Dimethylanilino)-2,6-diphenyltelluropyrylium Perchlorate A solution of p-bromo-N,N-dimethylaniline (1.00 g) in 5 ml of dry tetrahydrofuran was added to magnesium turnings (0.24 g) under an argon atmosphere. A small crystal of iodine was added and the resulting mixture was warmed at reflux for 2 hours. 2,6-Diphenyltelluropyrone (0.20 g) in 5 ml of dry tetrahydrofuran was added dropwise. The resulting mixture was stirred at reflux for an additional hour. The tetrahydrofuran solution was decanted from the magnesium turnings and concentrated. The residue was taken up in 5 ml of acetic acid. One ml of 70% perchloric acid was added. The resulting solution was added dropwise to 20 ml of cold water. The precipitate was collected by filtration and recrystallized from acetonitrile to give 0.26 g (81%) of a copper-bronze solid.

EXAMPLE 5

Preparation of Dye 5, Table I
4-(2,6-Diphenyl-4-thiapyranylidenemethyl)-2,6-diphenyltelluropyrylium Perchlorate 2,6-Diphenyltelluropyrone (0.50 g, 1.4 mmol) and 4-methyl-2,6-diphenylthiapyrylium perchlorate (0.50 g, 1.4 mmol) in 5 ml of acetic anhydride were warmed on a steam bath for 15 minutes and then chilled. The dye was collected by filtration and recrystallized from acetonitrile to give 0.85 g (88%) of copper-colored needles.

EXAMPLE 6

Preparation of Dye 18, Table II
4-(p-N,N-Dimethylaminostyryl)-7-methoxybenzotelluropyrylium Tetrafluoroborate N,N-Dimethylaminobenzaldehyde (0.50 g, 3.3 mmol) and 4-methyl-7-methoxybenzotelluropyrylium tetrafluoroborate (0.60 g, 1.3 mmol) in 5 ml of acetic anhydride were warmed on a steam bath for 3 minutes. Acetonitrile (10 ml) was added and the reaction mixture was chilled. The crude product was collected by filtration and recrystallized from acetonitrile to give 0.34 g (44%) of a golden-brown solid.

EXAMPLE 7

Preparation of Dye 23, Table II

A mixture of 1,3,3-trimethoxypropene (0.5 ml) and 4-methyl-7-methoxybenzotelluropyrylium trifluoromethanesulfonate (0.55 g, 1.0 mmol) in 2 ml of acetic anhydride, 1.5 ml of acetic acid, and 0.5 ml of pyridine was warmed on a steam bath for 1.5 minutes and was chilled. The crude product was collected by filtration and recrystallized from acetonitrile to give 0.22 g (49%) of a brown solid.

EXAMPLE 8

Preparation of
4-(2,6-Diphenyltelluropyranylidene)benzoylacetonatophosphorous Tetrafluoride (17)

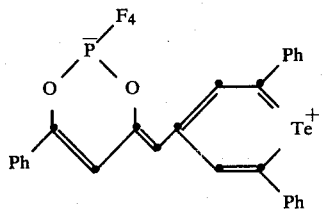

Benzoylacetonatophosphorous tetrafluoride (0.27 g 1.0 mmol) and 2,6-diphenyltelluropyrone (0.38 g, 1.1 mmol) in 3 mL of acetic anhydride were warmed on a steam bath for 20 minutes. Acetonitrile (3 mL) was added and the resulting mixture was chilled. The product was collected by filtration and recrystallized from acetonitrile to give 0.17 g (28%) of a metallic green solid.

EXAMPLE 9

The following illustrative examples show the use of the dyes, of the present invention as sensitizers in electrophotographic elements. Each film was formulated and coated as follows. Ten to fifteen mg of a dye from Tables I, II or III and 215 mg to 300 mg of tri-p-tolylamine were dissolved in 3 ml of dichloromethane. To this solution were added 4 ml of dichloromethane containing 12.5% Lexan-145 ™ (a bisphenol polycarbonate available from General Electric) by weight. The solution was stirred for several minutes and then coated at 0.006 mil wet thickness on a poly(ethylene terephthalate) support containing 0.4 OD evaporated nickel. After initial evaporation of the solvent, the films were dried 24 hr in air at 60° C. Dry thickness was about 7 μm.

The quantum efficiency ($\Phi_o$) of each film was measured as follows. Samples were corona-charged to a surface potential equivalent to the field strengths, $E_o$. They were then exposed to monochromatic radiation at the wavelength indicated in Table IV ($\lambda$, nm) with a bandwidth of 10 nm. The incident photon flux at this wavelength was measured with an Optronics Laboratories Model 730-A Radiometer. Films were allowed to discharge while exposed to the indicated radiation. The initial quantum efficiency (the number of electron-hole pairs produced per incident photon) at field strength $E_o$ was then determined by computation of the slope of the discharge curve at $E_o$. The photodischarge sensitivity at wavelength of irradiation ($S_{\frac{1}{2}}$), was also determined by allowing the films to discharge from $E_o$ to $E_o/2$. The amount of radiation necessary to produce this discharge was then calculated from the time required for this half-decay and the incident photon flux.

Dyes 1, 10, 11, 12 and 13 of Table I, Dye 10 of Table II and Dyes 1, 3, 5, 7, 8 and 9 of Table III were tested as described above. Each of the dyes resulted in an increase in the speed and/or quantum efficiency of the photoconductive layers in which they were included. The data from the tests are presented in Table IV.

TABLE IV

Telluropyrylium dyes as Sensitizers for Tri-p-tolylamine Photoconductors

| Film No. | Sensitizer | λ nm | $E_o$ V/cm | $\Phi_o$ | $S_{\frac{1}{2}}$ ergs/cm² |
|---|---|---|---|---|---|
| 1 | None | 350 | 1.6 × 10⁶ | 0.0094 | 1500 |
| 2 | No. 1, Table I | 760 | 3.3 × 10⁵ | 0.036 | 58 |
| 3 | No. 10, Table I | 630 | 6.1 × 10⁵ | 0.0063 | 315 |
|   |   | 670 | 4.9 × 10⁵ | 0.0044 | 271 |
| 4 | No. 11, Table I | 660 | 6.2 × 10⁵ | 0.008 | 135 |
|   |   | 715 | 4.5 × 10⁵ | 0.0052 | 169 |
| 5 | No. 12, Table I | 730 | 3.1 × 10⁵ | 0.0024 | 424 |
| 6 | No. 13, Table I | 780 | 4.4 × 10⁵ | 0.0015 | 823 |
| 7 | No. 10, Table II | 660 | 5.7 × 10⁵ | 0.011 | 193 |
| 8 | No. 7, Table III | 625 | 6.2 × 10⁵ | 0.0042 | 430 |
| 9 | No. 1 Table III | 800 | — | — | 1242 |
| 10 | No. 3 Table III | 605 | 5.8 × 10⁵ | 0.0046 | 202 |
| 11 | No. 5 Table III | 615 | 1.5 × 10⁶ | 0.14 | 44 |
| 12 | No. 8 Table III | 595 | 5.6 × 10⁵ | 0.0042 | 557 |
| 13 | No. 9 Table III | 620 | 1.2 × 10⁶ | 0.051 | 84 |

Film element 1 consisted of 30% tri-p-tolylamine by weight. Film elements of 2, 3, 4, 5, 6, 8, 9, 11 and 13 consisted of 1.5% sensitizer, 38.5% tri-p-tolylamine and 60% Lexan 145. Film element 7 consisted of 2% sensitizer, 30% tri-p-tolylamine and 68% Lexan 145. Film element 10 consisted of 2% sensitizer, 38% tri-p-tolylamine and 60% Lexan 145. Film element 12 consisted of 1% sensitizer, 39.5% tri-p-tolylamine and 60% Lexan 145.

Although the invention has been described in considerable detail with particular reference to certain preferred embodiments thereof, variations and modifications can be effected within the spirit and scope of the invention.

We claim:
1. A dye comprising a telluropyrylium nucleus.
2. A dye comprising a telluropyrylium nucleus having a structure

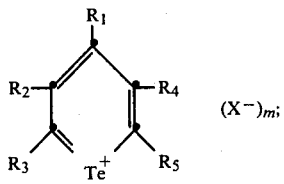

I.

$(X^-)_m$;

wherein
$R_1$, $R_3$ and $R_5$ each independently represent hydrogen, alkyl, alkylamino, dialkylamino, alkoxy, aryloxy, alkylaryl, aryl, heterocyclyl,

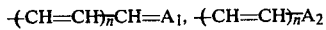

or a zwitterionic diketonate of the structure:

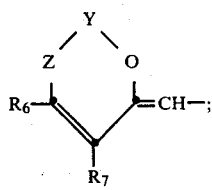

II.

wherein
$R_2$ and $R_4$ each independently represents hydrogen, aryl or alkyl; or
$R_2$ and $R_3$, or $R_4$ and $R_5$, taken together with the carbon atoms to which they are attached, form a mono- or polynuclear fused carbocyclic ring having from about 5 to 20 carbon atoms;
$R_6$ and $R_7$ each independently represents hydrogen, alkyl, aryl, heteroaryl or a mono- or polycyclic heterocyclylidene group, or $R_6$ and $R_7$ taken together with the carbon atoms to which they are attached, form a fused mono- or polycyclic, carbocyclic or heterocyclic group having from about 5 to 20 carbon atoms;
$A_1$ represents a mono- or polycyclic heterocyclylidene group;
$A_2$ represents hydrogen, alkyl, alkoxy, aryl, amino, dialkylaminoaryl, alkylamino, arylamino, dialkylamino, diarylamino or a mono- or polycyclic heterocyclyl group;
n represents a number from 0 to 5;
m represents 1, except when $R_1$, $R_3$ or $R_5$ is the zwitterionic group, m represents 0;
X represents an anion;
Y represents $BF_2$ or $PF_4$; and
Z represents O or S.
3. A dye according to claim 2 wherein $R_1$, $R_3$ and $R_5$ each independently represents hydrogen, methyl, ethyl, phenyl, p-N,N-dimethylaminophenyl, p-anisyl, phenoxy, ethoxy, methoxy,

$R_6$ and $R_7$ each independently represents hydrogen, methyl, phenyl, methoxyphenyl, p-N,N-dimethylaminophenyl, pyridyl, oxazolyl, thiazolyl, selenazolyl, pyranyl, thiapyranyl, selenapyranyl, telluropyranyl, or oxaindolazinyl or $R_6$ and $R_7$ are taken together with the carbon atoms to which they are attached to form a fused mono- or polycyclic, carbocyclic or heterocyclic group having from 5 to 20 carbon atoms;
$A_1$ represents a nucleus selected from the group consisting of oxazolylidene, thiazolylidene, selenazolylidene, imidazolylidene, pyranylidene, thiapyranylidene, selenapyranylidene, telluropyranylidene, oxaindolazinylidene, benzoxazolylidene, benzothiazolylidene, benzopyranylidene, benzothiapyranylidene, benzoselenapyranylidene, or benzotelluropyranylidene;
$A_2$ represents hydrogen, methyl, methoxy, ethoxy, phenyl, dimethylaminophenyl, dimethylamino or a nucleus selected from the group consisting of oxazolyl, 9-julolidyl, thiazolyl, selenazolyl, imidazolyl, pyryliumyl, thiapyryliumyl, selenapyrylium, telluropyrylium, pyrydinyl, furanyl, thiophenyl, selenophenyl, tellurophenyl, oxaindolazinyl, benzoxazolyl, benzothiazolyl, benzopyryliumyl, benzothiapyryliumyl, benzoselenapyryliumyl, benzotelluropyryliumyl or naphthyl;
X represents $BF_4$, $ClO_4$, $CF_3SO_3$, $FSO_3$, $PF_6$, $CH_3SO_3$, CL, Br, or I.
4. A dye comprising a benzotelluropyrylium nucleus.
5. A dye comprising a benzotelluropyrylium nucleus having a structure:

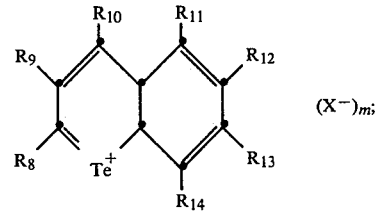

III.

$(X^-)_m$;

wherein,
$R_{10}$ and $R_8$ each independently represents hydrogen, alkyl, alkylamino, arylamino, alkoxy, aryloxy, dialkylamino, diarylamino,

or a zwitterionic diketonate of the structure:

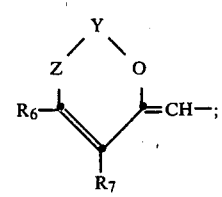

II.

$A_1$ represents a mono- or polycyclic heterocyclylidene group;

$A_2$ represents hydrogen, alkyl, alkoxy, aryl, dialkylaminoaryl, dialkylamino, alkylamino, arylamino or a mono- or polycyclic heterocyclyl group;

$R_6$ and $R_7$ each independently represents hydrogen, alkyl, aryl, heteroaryl, a mono- or polycyclic heterocyclylidene group or $R_6$ and R taken together with the carbon atom to which they are attached, form a fused mono- or polycyclic carbocyclic or heterocyclic group having from about 5 to 20 carbon atoms;

$R_9$, $R_{11}$, $R_{12}$, $R_{13}$ and R each independently represents hydrogen, alkyl, alkoxy, aryl, halogen, alkylamino or arylamino; or $R_{11}$ and $R_{12}$, $R_{12}$ and $R_{13}$ or $R_{13}$ and $R_{14}$, taken together with the carbon atoms to which they are attached, form a fused carbocyclic ring having from 5 to 20 carbon atoms;

n represents 0, 1 or 2;

m represents 1 except when $R_8$ or $R_{10}$ is the zwitterionic group, m represents 0;

X represents an anion;

Y represents $BF_2$ or $PF_4$; and

Z represents O or S.

6. A dye according to claim 5 wherein $R_8$ and $R_{10}$ each independently represent hydrogen, methyl, ethyl, methoxy, hydroxy, ethoxy, phenyl, phenoxy, p-anisyl, 2,5-dimethoxyphenyl, p-N,N-dimethylaminophenyl, $-(CH=CH)_{\overline{n}}CH=A_1$ or $-(CH=CH)_{\overline{n}}A_2$;

$A_1$ represents a nucleus selected from the group consisting of oxazolylidene, thiazolylidene, selenazolylidene, imidazolylidene, pyranylidene, thiapyranylidene, selenapyranylidene, telluropyranylidene, oxaindolazinylidene, benzoxazolylidene, benzothiazolylidene, benzopyranylidene, benzothiapyranylidene, benzoselenapyranylidene, or benzotelluropyranylidene;

$A_2$ represents hydrogen, methyl, methoxy, ethoxy, phenyl, dimethylaminophenyl, dimethylamino or a nucleus selected from the group consisting of oxazolyl, 9-julolidyl, thiazolyl, selenazolyl, imidazolyl, pyryliumyl, thiapyryliumyl, selenapyrylium, telluropyrylium, pyrydinyl, furanyl, thiophenyl, selenophenyl, tellurophenyl, oxaindolazinyl, benzoxazolyl, benzothiazolyl, benzopyryliumyl, benzothiapyryliumyl, benzoselenapyryliumyl, benzotelluropyryliumyl or naphthyl;

$R_6$ and $R_7$ each independently represents hydrogen, methyl, phenyl, methoxyphenyl, p-N,N-dimethylaminophenyl, aminophenyl, pyridyl, oxazolyl, thiazolyl, selenazolyl, pyranyl, thiapyranyl, selenapyranyl, telluropyranyl or oxindolazinyl; or $R_6$ and $R_7$ are taken together with the carbon atoms to which they are attached to form a fused naphthalene ring; and X represents $BF_4$, $ClO_4$, $CF_3SO_3$, $FSO_3$, $PF_6$, $CH_3SO_3$, Cl, Br or I.

7. A dye comprising a telluropyrylium nucleus selected from the group consisting of:

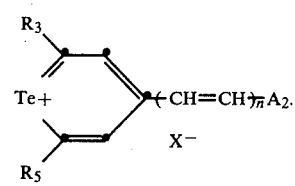

and

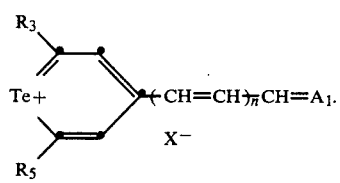

wherein $A_1$, $A_2$, n, $R_3$, $R_5$ and X for each dye is as defined below:

| Dye No. | $=A_1$ or $-A_2$ | $R_3$ | $R_5$ | n | $X^-$ |
|---|---|---|---|---|---|
| 1 | p-Me$_2$N—C$_6$H$_4$— | C$_6$H$_5$ | C$_6$H$_5$ | 0 | ClO$_4$ |
| 2 | p-Me$_2$N—C$_6$H$_4$— | C$_6$H$_5$ | C$_6$H$_5$ | 0 | BF$_4$ |
| 3 | p-Me$_2$N—C$_6$H$_4$— | C$_6$H$_5$ | C$_6$H$_5$ | 0 | CF$_3$SO$_3$ |
| 4 | Ph\O/Ph (dioxine) | C$_6$H$_5$ | C$_6$H$_5$ | 1 | BF$_4$ |
| 5 | Ph\S/Ph | C$_6$H$_5$ | C$_6$H$_5$ | 1 | ClO$_4$ |
| 6 | Ph\Se/Ph | C$_6$H$_5$ | C$_6$H$_5$ | 1 | ClO$_4$ |
| 7 | CH$_3$CH$_2$O— | C$_6$H$_5$ | C$_6$H$_5$ | 0 | FSO$_3$ |
| 8 | CH$_3$— | C$_6$H$_5$ | C$_6$H$_5$ | 0 | BF$_4$ |
| 9 | Ph\Te/Ph | C$_6$H$_5$ | C$_6$H$_5$ | 1 | BF$_4$ |
| 10 | Ph\O/Ph | C$_6$H$_5$ | C$_6$H$_5$ | 0 | BF$_4$ |

| Dye No. | =A₁ or —A₂ | R₃ | R₅ | n | X⁻ |
|---|---|---|---|---|---|
| 11 | Ph-S-Ph (ring) | C₆H₅ | C₆H₅ | 0 | ClO₄ |
| 12 | Ph-Se-Ph (ring) | C₆H₅ | C₆H₅ | 0 | ClO₄ |
| 13 | Ph-Te-Ph (ring) | C₆H₅ | C₆H₅ | 0 | BF₄ |
| 14 | p-Me₂N—C₆H₄— | C₆H₅ | C₆H₅ | 1 | BF₄ |
| 15 | p-Me₂N—C₆H₄— | C₆H₅ | C₆H₅ | 2 | BF₄ |
| 16 | (julolidine) | C₆H₅ | C₆H₅ | 1 | CF₃SO₃ |
| 17 | (tetrahydroquinoline) | C₆H₅ | C₆H₅ | 1 | CF₃SO₃ |
| 18 | CH₃— | C₆H₅ | C₆H₅ | 0 | BF₄ |
| 19 | CH₃CH₂O | C₆H₅ | C₆H₅ | 0 | FSO₃ |
| 20 | p-Me₂N—C₆H₄— | CH₃ | CH₃ | 0 | BF₄ |

8. A dye comprising a benzotelluropyrylium nucleus selected from the group of dyes consisting of:

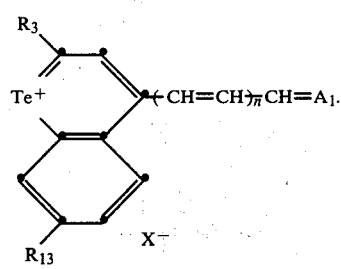

and

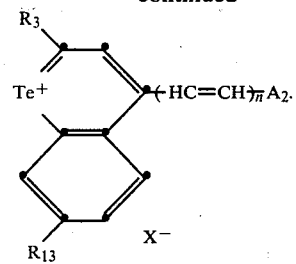

wherein A, n, R₃, R₈, R₁₃ and X for each dye is as defined below:

| Dye No. | =A₁ or —A₂ | R₃ | R₁₃ | n | X⁻ |
|---|---|---|---|---|---|
| 1 | H | C₆H₅ | CH₃O | 0 | ClO₄ |
| 2 | H | C₆H₅ | CH₃O | 0 | PF₆ |
| 3 | CH₃— | C₆H₅ | CH₃O | 0 | CF₃SO₃ |
| 4 | CH₃— | C₆H₅ | CH₃O | 0 | BF₄ |
| 5 | CH₃— | C₆H₅ | CH₃O | 0 | ClO₄ |
| 6 | CH₃— | C₆H₅ | CH₃O | 0 | ClO₄ |
| 7 | CH₃CH₂O— | C₆H₅ | CH₃O | 0 | FSO₃ |
| 8 | CH₃CH₂O— | CH₃ | CH₃O | 0 | FSO₃ |
| 9 | p-Me₂N—C₆H₄— | C₆H₅ | CH₃O | 0 | BF₄ |
| 10 | p-Me₂N—C₆H₄— | C₆H₅ | CH₃O | 0 | ClO₄ |
| 11 | p-Me₂N—C₆H₄— | C₆H₅ | CH₃O | 1 | CF₃SO₃ |
| 12 | p-Me₂N—C₆H₄— | C₆H₅ | CH₃O | 1 | BF₄ |
| 13 | p-Me₂N—C₆H₄— | C₆H₅ | CH₃O | 2 | CF₃SO₃ |
| 14 | Me₂N— | C₆H₅ | CH₃O | 1 | CF₃SO₃ |
| 15 | Ph-O-Ph (ring) | C₆H₅ | CH₃O | 0 | BF₄ |
| 16 | Ph-S-Ph (ring) | C₆H₅ | CH₃O | 0 | ClO₄ |
| 17 | Ph-Se-Ph (ring) | C₆H₅ | CH₃O | 0 | ClO₄ |
| 18 | (Ph,Te,OCH₃ benzo structure) | C₆H₅ | CH₃O | 1 | CF₃SO₃ |
| 19 | (Ph,Te,OCH₃ benzo structure) | C₆H₅ | CH₃O | 1 | ClO₄ |

-continued

| Dye No. | =A₁ or —A₂ | R₃ | R₁₃ | n | X⁻ |
|---|---|---|---|---|---|
| 20 | (structure: Ph-Te with methylene, OCH₃) | C₆H₅ | CH₃O | 1 | PF₆ |
| 21 | (structure: Ph-Te with OCH₃) | C₆H₅ | CH₃O | 1 | CF₃SO₃ |
| 22 | (structure: Ph-Te with methylene, OCH₃) | C₆H₅ | CH₃O | 2 | PF₆ |
| 23 | (structure: Ph-Te with OCH₃) | C₆H₅ | CH₃O | 2 | CF₃SO₃ |
| 24 | (structure: Ph-Te with methylene, OCH₃) | C₆H₅ | CH₃O | 3 | CF₃SO₃ |
| 25 | (structure: Ph-S benzothiopyran) | C₆H₅ | CH₃O | 1 | CF₃SO₃ |
| 26 | (structure: Ph-S benzothiopyran) | C₆H₅ | CH₃O | 2 | CF₃SO₃ |
| 27 | (indolizine structure) | C₆H₅ | CH₃O | 1 | BF₄ |
| 28 | (indolizine structure) | C₆H₅ | CH₃O | 1 | BF₄ |
| 29 | (julolidine structure) | C₆H₅ | CH₃O | 1 | PF₆ |
| 30 | C₆H₅— | | CH₃ | CH₃O | 0 | CF₃SO₃ |

9. A dye comprising a telluropyrylium nucleus and zwitterionic diketonate substituent selected from the group of dyes consisting of:

(structures showing various telluropyrylium dyes with PF₄ and BF₂ diketonate groups with Ph, Te⁺, and OCH₃ substituents)

-continued

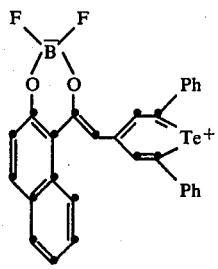

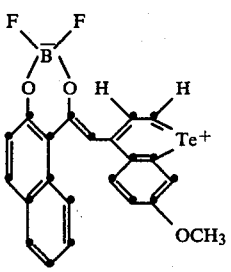

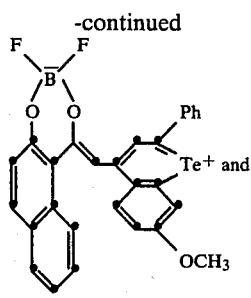

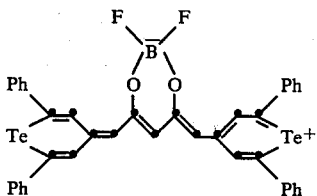

10. A photoconductive composition comprising an electron donating organic photoconductor and a sensitizing amount of a dye defined in claims 1, 2, 3, 4, 5, 6, 7, 8 or 9.

11. A photoconductive composition as in claim 10, wherein the dye is present in an amount of from 0.001 to 30% based on the weight of the composition.

12. A photoconductive composition as in claim 10, wherein the electron donating photoconductor comprises a tertiary amine.

13. A photoconductive composition as in claim 10, wherein the electron donating photoconductor comprises a triarylamine.

14. A photoconductive element comprising a support having a layer containing an electron donating organic photoconductor and a sensitizing amount of a dye defined in claims 1, 2, 3, 4, 5, 6, 7, 8 or 9.

15. A method of sensitizing an electron donating photoconductive composition comprising adding a sensitizing amount of a telluropyrylium dye defined in claims 1, 2, 3, 4, 5, 6, 7, 8 or 9 to the photoconductive composition.

* * * * *